United States Patent [19]

Matsuishi et al.

[11] Patent Number: 4,808,596
[45] Date of Patent: Feb. 28, 1989

[54] IMIDAZO[4,5-B]PYRIDINE COMPOUNDS AND PHARMACEUTICAL COMPOSITIONS CONTAINING SAME

[75] Inventors: Naoto Matsuishi, Kawaguchi; Haruki Takeda, Kamisato; Kenichi Iizumi, Mitaka; Kiyokazu Murakami, Yokohama; Akira Hisamitsu, Omiya, all of Japan

[73] Assignee: Tokyo Tanabe Company, Ltd., Japan

[21] Appl. No.: 77,686

[22] Filed: Jul. 24, 1987

[30] Foreign Application Priority Data

Jul. 25, 1986 [JP] Japan .................... 61-173551
May 30, 1987 [JP] Japan .................... 62-133534

[51] Int. Cl.$^4$ .................. A61K 31/435; C07D 471/04
[52] U.S. Cl. ........................... 514/303; 546/118
[58] Field of Search .................... 546/118; 514/303

[56] References Cited

FOREIGN PATENT DOCUMENTS 0187977 7/1986 European Pat. Off. .

Primary Examiner—Alan L. Rotman
Assistant Examiner—Bernard I. Dentz
Attorney, Agent, or Firm—McGlew and Tuttle

[57] ABSTRACT

Imidazo[4,5-b]pyridine compounds of the general formula [I] are provided:

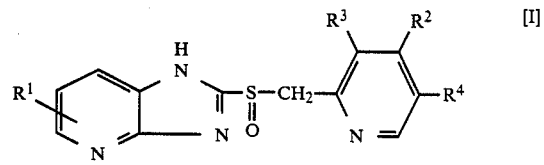

where $R^1$ is straight-chain or branched $C_{1-8}$ alkoxy which may be substituted with cycloalkyl, or $C_{2-4}$ fluoroalkyloxy, $R^2$ is H, methyl or methoxy, and $R^3$ and $R^4$ are each H or methyl and may be the same or different. All these compounds have good activity of inhibiting potassium ion-dependent adenosine triphosphatase and excellent storage stability, so that they are usable for the treatment of gastric and/or duodenal ulcers.

13 Claims, No Drawings

IMIDAZO[4,5-B]PYRIDINE COMPOUNDS AND PHARMACEUTICAL COMPOSITIONS CONTAINING SAME

BACKGROUND OF THE INVENTION (1) Field of the Invention

This invention relates to novel imidazo[4,5-b]-pyridine compounds. The imadazo[4,5-b]pyridine compounds of this invention have excellent storage stability and can be used as drugs for the treatment of gastric and duodenal ulcers.

(2) Description of the Prior Art

In recent pathophysiological studies on gastric and duodenal ulcers, attention has been focused on the behavior of potassium ion-dependent adenosine triphosphase [hereinafter referred to as $(H^+ + K^+)$ ATPase] participating in the production of hydrocholoric acid in the vesicles of the gastric endoplasmic reticulum, and the presence of an inhibitory effect on this enzyme is now considered to be a criterion of the usefulness of anti-ulcer agents (Gastroenterology, Vol. 1, p. 420, 1943; ibid., Vol. 73, p. 921, 1977). From this point of view, a class of compounds having a side chain comprising an unsubstituted to trisubstituted pyridylmethylsulfinyl group are now being developed as anti-ulcer agents, and one typical example thereof is Omeprazole having a benzimidazole skeleton (Japanese Patent Laid-Open No. 141783/'79; British Medical Journal, Vol. 287, p. 12, 1983). On the other hand, it has been confirmed or suggested that certain imidazopyridine compounds have an inhibitory effect on the aforesaid enzyme. Typical examples thereof are compounds of the general formula

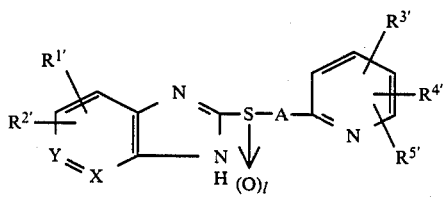

where one of X and Y is $=CH-$ and the other is $=N-$, $R^{1'}$ and $R^{2'}$ are each a hydrogen atom, a lower alkoxycarbonyl group, a halogen atom, a lower alkyl group, an amino group or a hydroxyl group and may be the same or different, $R^{3'}$, $R^{4'}$ and $R^{5'}$ are each a hydrogen atom, a lower alkoxy group or a lower alkyl group and may be the same or different, A is a lower alkylene group, and l is 0 or 1. However, when Y is $=CH-$, X is $=N-$, and l is 0, all of $R^{3'}$, $R^{4'}$ and $R^{5'}$ should not be hydrogen atoms. These compounds are reported in Japanese Patent Laid-Open No. 145182/'86 and will hereinafter be referred to tentatively as the well-known imidazopyridine compounds.

However, it has been found that, when stored without any preventive measure, Omeprazole undergoes a higher degree of deterioration than might be expected. In order to overcome its low storage stability, it has been imperative to convert Omeprazole into its alkali salt (Japanese Patent Laid-Open No. 167587/'84).

As to the well-known imidazopyridine compounds, the present inventors chose, as two typical examples thereof, 2-[2-(3,5-dimethyl-4-methoxy)pyridylmethylsulfinyl]-6-bromoimidazo[4,5-b]pyridine (hereinafter referred to tentatively as Compound α) and 2-[2-(3,5-dimethyl-4-methoxy)pyridylmethylsulfinyl]-6-methylimidazo[4,5-b]-pyridine (hereinafter referred to tentatively as Compound β), and subjected them to various tests. As a result, it has been found that (1) similarly to Omeprazole, these compounds are also defective in storage stability and (2) while they exhibit a marked inhibitor effect on $(H^+ + K^+)$ ATPase in the in vitro tests, this effect is not satisfactorily reflected in the in vivo tests for inhibitory effect on gastric secretion and for inhibitory effects on various experimental ulcers.

SUMMARY OF THE INVENTION

In view of these circumstances, the present inventors have made an exhaustive study of compounds related to the aforesaid well-known imidazopyridine compounds and have discovered that compounds obtained by substituting various alkoxy groups for the bromine atom or methyl group of Compounds α and β have excellent storage stability and exhibit a good anti-ulcer effect in various in vivo tests. The present invention has been completed on the basis of this discovery.

According to one feature of the present invention, there are provided imidazo[4,5-b]pyridine compounds of the general formula

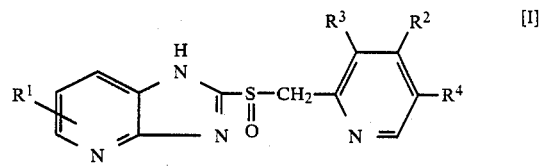

where $R^1$ is a straight-chain or branched alkoxy group of 1 to 8 carbon atoms which may be substituted with a cycloalkyl group, or a fluoroalkyloxy group of 2 to 4 carbon atoms, $R^2$ is a hydrogen atom, a methyl group or a methoxy group, and $R^3$ and $R^4$ are each a hydrogen atom or a methyl group and may be the same or different.

According to another feature of the present invention, there are provided processes for preparing imidazo[4,5-b]pyridine compounds represented by the above geneal formula [I].

According to still another feature of the present invention, there are provided pharmaceutical compositions, containing an imidazo[4,5-b]pyridine compound represented by the above general formula [I], as an active ingredient.

It is to be understood that the imidazo[4,5-b]pyridine compounds represented by the general formula [I] also include their tautomers represented by the general formula

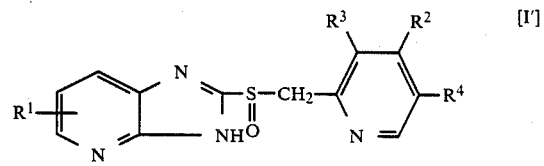

where $R^1$, $R^2$, $R^3$ and $R^4$ are as previously defined.

In the general formulas [I] and [I'], the alkoxy group represented by $R^1$ is selected from among methoxy, ethoxy, isopropyloxy, n-propyloxy, sec-butyloxy, isobutyloxy, tert-butyloxy, n-butyloxy, n-pentyloxy, 3-methylbutyloxy, n-hexyloxy, n-heptyloxy, 5-methylhexyloxy, 2,4,4-trimethylpentyloxy, n-octyloxy, cyclopropylmethyloxy, 1-cyclopropylethyloxy, cyclobutylmethyloxy, cyclopentylmethyloxy, 2-cyclopentylethyloxy, 3-cyclopentylpropyloxy, cyclohexylmethyloxy, 2-cyclohexylethyloxy and like groups. Similarly, the fluoroalkyloxy group represented by $R^1$ is selected from among 2,2,2-trifluoroethoxy, 2,2,3,3,3-pentafluoropropyloxy, 1,1,1,3,3,3-hexafluoro-2-propyloxy, 2,2,3,3,4,4,4-heptafluorobutyloxy and like groups.

DETAILED DESCRIPTION OF THE PREFERRED EMBODIMENTS

The imidazo[4,5-b]pyridine compounds represented by the above general formulas [I] and [I'] (hereinafter referred to briefly as the present compounds) can be prepared by oxidizing a sulfide compound of the general formula

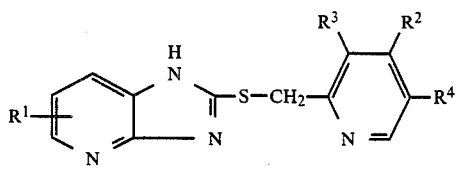
[II]

where $R^1$, $R^2$, $R^3$ and $R^4$ are as previously defined, in the presence of a suitable solvent and with the aid of an oxidizing agent. The oxidizing agent should be used in an amount of 1.0 to 1.3 moles per mole of the sulfide compound [II]. Oxidizing agents useful for this purpose include, for example, peroxides such as m-chloroperbenzoic acid, perbenzoic acid, peracetic acid and the like. However, m-chloroperbenzoic acid is preferred because of its high stability. Suitable reaction solvents include, for example, halogenated hydrocarbons such as chloroform, tetrachloroethane, etc.; alcohols such as methanol, ethanol, propanol, butanol, etc.; and mixtures of two or more such solvents. However, from the viewpoint of selectivity and yield in the oxidation reaction, it is particularly preferable to use chloroform or a mixture of chloroform and methanol. The reaction is carried out at a temperature of $-70°$ to $30°$ C., preferably $-20°$ to $10°$ C., for a period of time ranging approximately from 1 minute to 24 hours, preferably from 5 minutes to 1 hour.

The sulfide compounds represented by the above general formula [II] can be prepared by condensing a thiol compound of the general formula

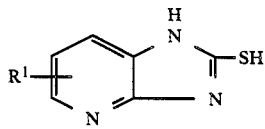
[III]

where $R^1$ is as previously defined, with a pyridine compound of the general formula

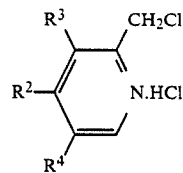
[IV]

where $R^2$, $R^3$ and $R^4$ are as previously defined, in a reaction solvent. This reaction may be carried out in the presence or absence of a base. If it is carried out in the absence of base, the resulting sulfide compound [II] is in the form of a hydrochloride and, therefore, needs to be dehydrochlorinated by means of a deacidifying agent. The pyridine compound [IV] should be used in an amount equimolar to the thiol compound [III], and the base should be used in an amount of 2.0 to 3.0 moles per mole of the thiol compound [III]. Bases useful for this purpose include, for example, sodium hydrogen carbonate, sodium carbonate, potassium carbonate, sodium hydroxide, potassium hydroxide and the like. Suitable reaction solvents include, for example, alcohols such as methanol, ethanol, propanol, butanol, etc.; aprotic polar solvents such as dimethylformamide, dimethyl sulfoxide, etc.; water; and mixtures of two or more such solvents. The reaction is carried out at a temperature of $10°$ to $200°$ C., preferably $60°$ to $80°$ C., for a period of time ranging approximately from 1 minute to 12 hours, preferably from 5 minutes to 4 hours. The thiol compound [III] used as a starting material can be prepared according to any of well-known processes including, for example, that described in The Journal of Organic Chemistry, Vol. 24, p. 1455, 1959.

Now, the beneficial effects of the present compounds [I] will be described hereinbelow. Specifically, they were tested for storage stability, in vitro inhibitory effect on $(H^+ + K^+)$ ATPase, and in vivo inhibitory effects on gastric secretion and on various experimental ulcers. The test compounds used for this purpose were the compounds enumerated below and considered to be typical examples of the present compounds [I]. The designation given in parentheses after the chemical name of each compound means its tentative name as used herein and corresponds to the respective one of the examples which will be described later.

2-[2-(3,5-Dimethyl)pyridylmethylsulfinyl]-5-methoxyimidazo[4,5-b]pyridine (Example 1).

2-[2-(3,5-Dimethyl-4-methoxy)pyridylmethylsulfinyl]-5-methoxyimidazo[4,5-b]pyridine (Example 2).

2-[2-(3,4,5-Trimethyl)pyridylmethylsulfinyl]-5-methoxyimidazo[4,5-b]pyridine (Example 3).

2-[2-(4-Methoxy-5-methyl)pyridylmethylsulfinyl]-5-methoxyimidazo[4,5-b]pyridine (Example 4).

2-[2-(4-Methoxy-5-methyl)pyridylmethylsulfinyl]-7-methoxyimidazo[4,5-b]pyridine (Example 7).

2-[2-(3,4,5-Trimethyl)pyridylmethylsulfinyl]-5-ethoxyimidazo[4,5-b]pyridine (Example 8).

2-[2-(3,5-Dimethyl)pyridylmethylsulfinyl]-5-isopropyloxyimidazo[4,5-b]pyridine (Example 10).

2-[2-(3,4,5-Trimethyl)pyridylmethylsulfinyl]-5-n-butyloxyimidazo[4,5-b]pyridine (Example 12).

2-[2-(4-Methoxy-5-methyl)pyridylmethylsulfinyl]-5-cyclopropylmethyloxyimidazo[4,5-b]pyridine (Example 13).

2-[2-(3,5-Dimethyl)pyridylmethylsulfinyl]-5-ethoxyimidazo[4,5-b]pyridine (Example 14).

2-[2-(3,5-Dimethyl-4-methoxy)pyridylmethylsulfinyl]-5-isopropyloxyimidazo[4,5-b]pyridine (Example 15).

2-[2-(4-Methoxy-5-methyl)pyridylmethylsulfinyl]-5-isopropyloxyimidazo[4,5-b]pyridine (Example 16).

2-[2-(4-Methoxy)pyridylmethylsulfinyl]-5-isopropyloxyimidazo[4,5-b]pyridine (Example 17).

2-[2-(3,5-Dimethyl)pyridylmethylsulfinyl]-5-n-propyloxyimidazo[4,5-b]pyridine (Example 18).

2-[2-(3,5-Dimethyl)pyridylmethylsulfinyl]-5-isobutyloxyimidazo[4,5-b]pyridine (Example 19).

2-[2-(3,5-Dimethyl-4-methoxy)pyridylmethylsulfinyl]-5-isobutyloxyimidazo[4,5-b]pyridine (Example 20).

2-[2-(4-Methoxy-5-methyl)pyridylmethylsulfinyl]-5-isobutyloxyimidazo[4,5-b]pyridine (Example 21).

2-[2-(4-Methoxy)pyridylmethylsulfinyl]-5-isobutyloxyimidazo[4,5-b]pyridine (Example 22).

2-[2-(3,5-Dimethyl)pyridylmethylsulfinyl]-5-cyclopropylmethyloxyimidazo[4,5-b]pyridine (Example 23).

2-[2-(3,5-Dimethyl-4-methoxy)pyridylmethylsulfinyl]-5-cyclopropylmethyloxyimidazo[4,5-b]pyridine (Example 24).

2-[2-(4-Methoxy)pyridylmethylsulfinyl]-5-cyclopropylmethyloxyimidazo[4,5-b]pyridine (Example 25).

2-[2-(3,5-Dimethyl-4-methoxy)pyridylmethylsulfinyl]-5-(2,2,2-trifluoroethoxy)imidazo[4,5-b]pyridine (Example 26).

2-[2-(4-Methyl)pyridylmethylsulfinyl]-5-(2,2,3,3,4,4,4-heptafluorobutyloxy)imidazo[4,5-b]pyridine (Example 30).

2-[2-(3,5-Dimethyl)pyridylmethylsulfinyl]-5-n-heptyloxyimidazo[4,5-b]pyridine (Example 33).

2-[2-(3,5-Dimethyl)pyridylmethylsulfinyl]-5-(3-methylbutyloxy)imidazo[4,5-b]pyridine (Example 34).

2-[2-(3,5-Dimethyl-4-methoxy)pyridylmethylsulfinyl]-6-(3-cyclopentylpropyloxy)imidazo[4,5-b]pyridine (Example 36).

(i) Storage stability

The storage stability of the present compounds [I] was tested by allowing each test compound to stand under severe conditions (i.e., a temperature of 60° C. and a relative humidity of 75%) for 8 days and then determining its percentage of residue according to a thin-layer densitometric method (Bunseki Kagaku, Vol. 23, No. 9, p. 1016, 1974). More specifically, upon completion of the severe treatment, 100 μg of each test compound was applied to a thin-layer plate and this plate was developed with a chloroform-ethanol mixture (volume ratio 10:1). The thin-layer plate used for this purpose was a TLC Plate Aluminum Oxide 60F$_{254}$ (manufactured by Merck Co.; 0.25 mm in thickness and 20 cm×20 cm in size), and it was developed over a distance of 15 cm. Then, using a Shimazu Two-wavelength Chromatoscanner CS-910 (manufactured by Shimazu Seisakusho), the resulting spot was analyzed at a wavelength of 300–315 nm.

The results thus obtained are shown in Table 1. For purposes of comparison, the percentages of residue of Omeprazole (at a measuring wavelength of 300 nm) and Compounds α and β (at a measuring wavelength of 310 nm) were determined in the same manner as described above and are also shown in Table 1.

TABLE 1

| Test compound | Storage stability (after treatment at 60° C. and 75% RH for 8 days) Percentage of residue |
|---|---|
| Omeprazole | 3 |
| Compound α | 0 |
| Compound β | 9 |
| Example 1 | 98 |
| Example 2 | 77 |
| Example 3 | 99 |
| Example 4 | 98 |
| Example 7 | 53 |
| Example 8 | 96 |
| Example 10 | 92 |
| Example 12 | 76 |
| Example 13 | 88 |
| Example 14 | 93 |
| Example 15 | 87 |
| Example 16 | 90 |
| Example 17 | 75 |
| Example 18 | 85 |
| Example 19 | 78 |
| Example 20 | 72 |
| Example 21 | 69 |
| Example 22 | 57 |
| Example 23 | 95 |
| Example 24 | 94 |
| Example 25 | 51 |
| Example 26 | 92 |
| Example 30 | 73 |
| Example 33 | 89 |
| Example 34 | 76 |
| Example 36 | 68 |

As is evident from Table 1, it can be recognized that the present compounds [I] have much better storage stability than Omeprazole and Compounds α and β.

(ii) Inhibitory effect on (H$^+$+K$^+$) ATPase

The inhibitory effect of the present compounds [I] on (H$^+$+K$^+$) ATPase was tested by adding each test compound to a solution containing 300–500 μg, on a protein basis, of the enzyme, incubating this reaction mixture at 35°–37° C. for 5–30 minutes, and then determining the residual activity of (H$^+$+K$^+$) ATPase present in the reaction mixture. The test compounds were dissolved in methanol or ethanol in advance and added to the reaction system in such an amount as to give a concentration of $1 \times 10^{-3}$ M. The (H$^+$+K$^+$) ATPase used in this test was prepared from fresh pieces of the fundus ventriculi of hog stomach according to the method of Saccomani et al. (The Journal of Biological Chemistry, Vol. 251, No. 23, p. 7690, 1976). The residual activity of (H$^+$+K$^+$) ATPase was determined by mixing magnesium chloride and potassium chloride with the incubated reaction mixture, adding adenosine triphosphate thereto, incubating this assay mixture 37° C. for 5–15 minutes to effect an enzymic reaction, and colorimetrically determining the liberated inorganic phosphate by use of an ammonium molybdate reagent. The initial concentrations of magnesium chloride, potassium chloride and adenosine triphosphate were adjusted to 2 mM, 20 mM and 2 mM, respectively. Colorimetric determinations were made at a wavelength of 360–400 nm. As a control experiment, the residual activity of (H$^+$+K$^+$) ATPase was determined by repeating the above-described procedure without adding any test compound to the reaction system. The results thus obtained are shown in Table 2. In this table, the inhibitory effect is indicated by the degree of inhibition which was obtained by calculating the difference between the measured value obtained in the control experiment and the measured value resulting from the addition of each test compound and expressing this difference as a percentage of the measured value obtained in the control experiment. For purposes of comparison, the inhibitory effect of Omeprazole and Compounds α and β on ($H^+ + K^+$) ATPase was tested in the same manner as described above and the results thus obtained are also shown in Table 2.

TABLE 2

| Test compound | Inhibitory effect on ($H^+ + K^+$) ATPase (at $1 \times 10^{-3}$ M) Degree of inhibition (%) |
|---|---|
| Omeprazole | 38.7 |
| Compound α | 100 |
| Compound β | 100 |
| Example 1 | 100 |
| Example 2 | 96.6 |
| Example 3 | 100 |
| Example 4 | 100 |
| Example 7 | 98.8 |
| Example 8 | 100 |
| Example 10 | 90.0 |
| Example 12 | 98.5 |
| Example 13 | 87.4 |
| Example 14 | 100 |
| Example 15 | 98.5 |
| Example 16 | 96.1 |
| Example 17 | 93.7 |
| Example 18 | 92.3 |
| Example 19 | 100 |
| Example 20 | 100 |
| Example 21 | 97.4 |
| Example 22 | 94.6 |
| Example 23 | 100 |
| Example 24 | 100 |
| Example 25 | 92.9 |
| Example 26 | 100 |
| Example 30 | 92.1 |
| Example 33 | 95.4 |
| Example 34 | 98.5 |
| Example 36 | 93.0 |

As is evident from Table 2, it can be recognized that the in vitro inhibitory effect of the present compounds [I] on ($H^+ + K^+$) ATPase is much better than that of Omeprazole and is comparable to that of Compounds α and β.

(iii) Inhibitory effect on gastric acid secretion

The inhibitory effect of the present compounds [I] on gastric acid secretion was tested by using male Wistar rats, weighing about 200 g, in groups of five. To these rats which had been fasted overnight, the test compounds were orally administered in a series of appropriately selected doses ranging from 1 to 100 mg/kg. Then, the pyloric end of the stomach was ligated. After the lapse of 4 hours, the total acidity of gastric juice of each rat was measured. More specifically, the test compounds were suspended in a 0.5% aqueous solution of carboxymethyl cellulose and administered to the rats 30 minutes before ligation. Gastric juice was collected by sacrificing and laparotomizing each rat. The total acidity of gastric juice was determined by titrating the gastric juice with a 0.1 N aqueous solution of sodium hydroxide until a pH of 7.0 was reached. As a control experiment, the total acidity of gastric juice of an untreated group was determined in the same manner as described above. The inhibitory effect of the test compounds on gastric acid secretion was evaluated on the basis of the dose (in mg/kg) required to inhibit gastric acid secretion, i.e. the total acidity of gastric juice, by 50% (hereinafter referred to as $ED_{50}$). The $ED_{50}$ value of each test compound was determined by calculating the difference in total acidity between the untreated group and each treated group, dividing the difference by the total acidity of the untreated group to obtain the degree of inhibition, and constructing a dose-response curve on the basis of the data thus obtained. The results are shown in Table 3. For purposes of comparison, the $ED_{50}$ values of Omeprazole and Compounds α and β were determined in the same manner as described above and are also shown in Table 3.

TABLE 3

| Test compound | Inhibitory effect on gastric acid secretion (p.o.) $ED_{50}$ (mg/kg) |
|---|---|
| Omeprazole | 35 |
| Compound α | 73 |
| Compound β | 41 |
| Example 1 | 13 |
| Example 2 | 18 |
| Example 3 | 9 |
| Example 4 | 15 |
| Example 7 | 22 |
| Example 8 | 12 |
| Example 10 | 19 |
| Example 12 | 21 |
| Example 13 | 18 |
| Example 14 | 15 |
| Example 15 | 13 |
| Example 16 | 16 |
| Example 17 | 17 |
| Example 18 | 19 |
| Example 19 | 11 |
| Example 20 | 10 |
| Example 21 | 13 |
| Example 22 | 15 |
| Example 23 | 12 |
| Example 24 | 9 |
| Example 25 | 18 |
| Example 26 | 15 |
| Example 30 | 19 |
| Example 33 | 17 |
| Example 34 | 14 |
| Example 36 | 19 |

As is evident from Table 3, it can be recognized that the present compounds [I] exhibit a more marked in vivo inhibitory effect on gastric acid secretion than Compounds α and β.

(iv) Inhibitory effects on various experimental ulcers

The inhibitory effects of the present compounds [I] on various experimental ulcers were tested by using male Wistar rats, weighing about 200 g, in groups of six and determining the respective ulceration indexes for 5 types of experimental ulcers. In each test, the test compounds were suspended in a 0.5% aqueous solution of carboxymethyl cellulose and administered orally in a series of appropriately selected doses ranging from 1 to 100 mg/kg. The test procedures for 5 types of experimental ulcers were as follows:

(Shay's ulcer)

In rats which had been fasted for 48 hours, the pyloric end of the stomach was ligated and they were maintained for 14 hours without giving any food or water. Then, each rat was sacrificed and the area of the ulcer(s) formed in the forestomach part was measured. The ulceration index was calculated on the basis of the data thus obtained. The test compounds were administered 30 minutes before ligation.

(Water-immersion stress ulcer)

Rats which had been fasted for 15 hours were immobilized in stress cages and immersed chest-deep in a water bath at 21° C. After 10 hours, each rat was sacrificed and the length of the ulcer(s) formed in the glandular stomach part was measured. The ulceration index was calculated on the basis of the data thus obtained. The test compounds were administered 10 minutes before exposure to the stress.

(Hydrochloric acid-ethanol ulcer)

To rats which had been fasted for 24 hours, a 150 mM hydrochloric acid-60% ethanol mixture was orally administered in an amount of 0.5 ml per 100 g of body weight. After an hour, each rat was sacrificed and the length of the ulcer(s) formed in the glandular stomach part was measured. The ulceration index was calculated on the basis of the data thus obtained. The test compounds were administered 30 minutes before administration of the hydrochloric acid-ethanol mixture.

(Indomethacin ulcer)

To rats which had been fasted for 24 hours, indomethacin was subcutaneously administered in a dose of 25 mg/kg. After 7 hours, each rat was sacrificed and the length of the ulcer(s) formed in the glandular stomach part was measured. The ulceration index was calculated on the basis of the data thus obtained. The test compounds were administered 30 minutes before administration of indomethacin.

(Aspirin ulcer)

In rats which had been fasted for 24 hours, the pyloric end of the stomach was ligated. After 5 minutes, aspirin was orally administered thereto in a dose of 150 mg/kg. Seven hours after ligation, each rat was sacrificed and the length of the ulcer(s) formed in the glandular stomach part was measured. The ulceration index was calculated on the basis of the data thus obtained. The test compounds were administered 30 minutes before ligation.

The pharmacological effect of the test compounds on each of the aforesaid experimental ulcers was evaluated on the basis of the dose (in mg/kg) required to inhibit the formation of ulcers by 50% (hereinafter referred to as $ID_{50}$). The $ID_{50}$ value of each test compound was determined by calculating the difference in ulceration index between the untreated group and each treated group, dividing the difference by the ulceration index of the untreated group to obtain the degree of inhibition, and constructing a dose-response curve on the basis of the data thus obtained. The results are shown in Table 4. For purposes of comparison, the $ID_{50}$ values of Omeprazole and Compounds α and β were determined in the same manner as described above and are also shown in Table 4.

TABLE 4

| Experimental ulcer | Test compound Inhibitory effects on various experimental ulcers, $ID_{50}$ (mg/kg) | | | | | | | | |
|---|---|---|---|---|---|---|---|---|---|
| | Omeprazole | Compound α | Compound β | Example 1 | Example 8 | Example 13 | Example 24 | Example 26 | Example 33 |
| Shay's ulcer | 30.3 | 100 or greater | 42.0 | 11.0 | 15.1 | 17.4 | 10.8 | 14.7 | 19.2 |
| Water-immersion stress ulcer | 39.7 | 100 or greater | 63.3 | 26.4 | 34.2 | 37.3 | 27.0 | 30.5 | 35.1 |
| Hydrochloric acid-ethanol ulcer | 13.6 | 63.3 | 25.4 | 5.1 | 8.2 | 9.6 | 3.5 | 7.9 | 10.3 |
| Indomethacin ulcer | 24.7 | 78.4 | 29.5 | 12.9 | 18.8 | 21.9 | 13.1 | 15.8 | 23.2 |
| Aspirin ulcer | 17.2 | 100 or greater | 23.8 | 6.3 | 10.7 | 14.5 | 5.4 | 9.5 | 12.6 |

As is evident from Table 4, it can be recognized that the present compounds [I] have a very good inhibitory effect on various types of ulcers.

(v) Toxicity test

The acute toxicity ($LD_{50}$) of several typical examples of the present compounds [I] (i.e., the compounds of Examples 1, 8, 13, 19, 24, 26 and 33) was tested with 5-weeks-old male Wistar rats. The $LD_{50}$ values of all compounds were greater than 4000 mg/kg in the case of oral administration, and greater than 500 mg/kg in the case of intraperitoneal administration. When Omeprazole was administered orally, its $LD_{50}$ value was greater than 4000 mg/kg.

In consideration of the results of the above-descirbed tests, the present compounds [I] may be said to be potent drugs useful for the treatment of gastric and duodenal ulcers and scarcely susceptible to inactivation during storage.

The present compounds [I] can be admixed with conventional pharmaceutical carriers to form various types of pharmaceutical compositions including solid preparations such as tablets, capsules, granules, powders fine granules, etc., and liquid preparations such as injectable solutions, syrups, elixirs, suspensions, emulsions, etc. Solid preparations may be coated so as to provide them with enteric coatings. Liquid preparations may be made by reacting one of the present compounds [I] with an alkali to form a physiologically acceptable salt thereof and then dissolving this salt in water, or by dissolving one of the present compounds [I] in an aqueous solution of an alkali. The pharmaceutical carriers used for these purposes may be selected according to the desired dosage form, Examples of the pharmaceutical carriers include excipients, binders and disintegrants, such as corn starch, dextrin, α-, β- or γ-cyclodextrin, glucose, lactose, sucrose, methylcellulose, ethylcellulose, calcium carboxymethylcellulose, crystalline cellulose, magnesium stearate, sodium alginate, Witepsol W35, Witepsol E85, polyvinyl alcohol, synthetic aluminum silicate, etc.; lubricants and coating agents such as talc, waxes, hydroxypropyl cellulose, hydroxypropyl methylcellulose, hydroxyethyl methylcellulose, cellulose acetate phthalate, hydroxypropyl methylcellulose phthalate, polyvinyl alcohol phthalate, styrene-maleic anhydride copolymer, polyvinyl acetal diethylaminoacetate, etc.; solubilizing agents such as glycerol, propylene glycol, mannitol, etc.; emulsifying or suspending agents such as polyoxyethylene stearate, polyoxyethylene cetyl alcohol ether, polyethylene glycol, polyvinyl pyrrolidone, etc.; stabilizers such as sorbitol, Tween 80, Span 60, fats and oils, etc.; and various solvents.

The dosage level of the present compounds [I] varies with the age of the patient, the severity of the disease, and the like. However, they are usually used in a daily dose of 0.5 to 2000 mg, preferably 3 to 200 mg, for adults. This daily dose may be administered in one to six divided doses, preferably in one to three divided doses.

The present invention is further illustrated by the following Reference Examples and Examples. The Reference Examples illustrates the preparation of sulfide compounds [II].

Reference Example A 1.81 g (0.01 mole) of 2-mercapto-5-methoxyimidazo[4,5-b]pyridine and 1.92 g (0.01 mole) of 2-chloromethyl-3,5-dimethylpyridine hydrochloride were added to 100 ml of ethanol containing 1.12 g (0.02 mole) of potassium hydroxide, and this mixture was heated under reflux for 2 hours. Upon cooling to room temperature, the resulting reaction solution was filtered to remove any insoluble matter, and the filtrate was concentrated under reduced pressure. The resulting residue was dissolved in 500 ml of chloroform, and this solution was washed with water, dried over anhydrous sodium sulfate and then evaporated to dryness under reduced pressure. The resulting residue was subjected to silica gel column chromatography using chloroform as the developing solvent. Thus, there was obtained 2.20 g (73.3% yield) of 2-[2-(3,5-dimethyl)pyridylmethylthio]-5-methoxyimidazo[4,5-b]pyridine in the form of colorless crystals having a melting point of 175°–176° C.

The following 24 compounds were prepared in substantially the same manner as described above, except that the 2-mercapto-5-methoxyimidazo[4,5-b]pyridine was replaced by 0.01 mole of each of the corresponding thiol compounds [III] and the 2-chloromethyl-3,5-dimethylpyridine hydrocholride was replaced by 0.01 mole of each of the corresponding pyridine compounds [IV].

2-[2-(3,5-Dimethyl-4-methoxy)pyridylmethylthio]-5-methoxyimidazo[4,5-b]pyridine, m.p. 154°–155° C.

2-[2-(3,4,5-Trimethyl)pyridylmethylthio]-5-methoxyimidazo[4,5-b]pyridine, m.p. 150°–151° C.

2-[2-(4-Methoxy-5-methyl)pyridylmethylthio]-5-methoxyimidazo[4,5-b]pyridine, m.p. 160°–162° C.

2-[2-(4-Methyl)pyridylmethylthio]-5-methoxyimidazo[4,5-b]pyridine, m.p. 134°–137° C.

2-[2-(3,5-Dimethyl)pyridylmethylthio]-6-methoxyimidazo[4,5-b]pyridine, glassy material.

2-[2-(4-Methoxy-5-methyl)pyridylmethylthio]-7-methoxyimidazo[4,5-b]pyridine, glassy material.

2-[2-(3,4,5-Trimethyl)pyridylmethylthio]-5-ethoxyimidazo[4,5-b]pyridine, m.p. 127°–128° C.

2-[2-(3,4,5-Trimethyl)pyridylmethylthio]-7-ethoxyimidazo[4,5-b]pyridine, m.p. 132°–136° C.

2-[2-(3,5-Dimethyl)pyridylmethylthio]-5-isopropyloxyimidazo[4,5-b]pyridine, m.p. 159°–160° C.

2-[2-(4-Methyl)pyridylmethylthio]-5-sec-butyloxyimidazo[4,5-b]pyridine, glassy material.

2-[2-(3,4,5-Trimethyl)pyridylmethylthio]-5-n-butyloxyimidazo[4,5-b]pyridine, m.p. 119°–120° C.

2-[2-(4-Methoxy-5-methyl)pyridylmethylthio]-5-cyclopropylmethyloxyimidazo[4,5-b]pyridine, m.p. 159°–161° C.

2-[2-(3,5-Dimethyl)pyridylmethylthio]-5-ethoxyimidazo[4,5-b]pyridine, m.p. 146°–147° C.

2-[2-(3,5-Dimethyl-4-methoxy)pyridylmethylthio]-5-isopropyloxyimidazo[4,5-b]pyridine, m.p. 130°–133° C.

2-[2-(4-Methoxy-5-methyl)pyridylmethylthio]-5-isopropyloxyimidazo[4,5-b]pyridine, m.p. 92°–94° C.

2-[2-(4-Methoxy)pyridylmethylthio]-5-isopropyloxyimidazo[4,5-b]pyridine, m.p. 134°–136° C.

2-[2-(3,5-Dimethyl)pyridylmethylthio]-5-n-propyloxyimidazo[4,5-b]pyridine, m.p. 116°–117° C.

2-[2-(3,5-Dimethy)pyridylmethylthio]-5-isobutyloxyimidazo[4,5-b]pyridine, m.p. 139°–141° C.

2-[2-(3,5-Dimethyl-4-methoxy)pyridylmethylthio]-5-isobutyloxyimidazo[4,5-b]pyridine, m.p. 132°–135° C.

2-[2-(4-Methoxy-5-methyl)pyridylmethylthio]-5-isobutyloxyimidazo[4,5-b]pyridine, m.p. 153°–154° C.

2-[2-(4-Methoxy)pyridylmethylthio]-5-isobutyloxyimidazo[4,5-b]pyridine, m.p. 119°–122° C.

2-[2-(3,5-Dimethyl)pyridylmethylthio]-5-cyclopropylmethyloxyimidazo[4,5-b]pyridine, m.p. 126°–128° C.

2-[2-(3,5-Dimethyl-4-methoxy)pyridylmethylthio]-5-cyclopropylmethyloxyimidazo[4,5-b]pyridine, m.p. 150°–153° C.

2-[2-(4-Methoxy)pyridylmethylthio]-5-cyclopropylmethyloxyimidazo[4,5-b]pyridine, m.p. 115°–117° C.

REFERENCE EXAMPLE B 2.50 g (0.01 mole) of 2-mercapto-5-(2,2,2-trifluoroethoxy)imidazo[4,5-b]pyridine and 2.22 g (0.01 mole) of 2-chloromethyl-4-methoxy-3,5-dimethylpyridine hydrochloride were added to 100 ml of ethanol, and this mixture was stirred at 60° C. for 2 hours. After the resulting reaction solution was concentrated under reduced pressure, 150 ml of a saturated aqueous solution of sodium hydrogen carbonate was added to the residue. This mixture was stirred and then extracted with 300 ml of chloroform. The extract thus obtained was dried over anhydrous sodium sulfate and then evaporated to dryness under reduced pressure. The desired product was isolated and purified by subjecting the resulting residue to silica gel column chromatography using a 50:1 mixture of chloroform and ethanol as the developing solvent. Thus, there was obtained 3.25 g (81.5% yield) of 2-[2-(3,5-dimethyl-4-methoxy)pyridylmethylthio]-5-(2,2,2-trifluoroethoxy)imidazo-[4,5-b]pyridine in the form of colorless crystals having a melting point of 178°–180° C.

The following 11 compounds were prepared in substantially the same manner as described above, except that the 2-mercapto-5-(2,2,2-trifluoroethoxy)imidazo[4,5-b]pyridine was replaced by 0.01 mole of each of the corresponding thiol compounds [III] and the 2-chloromethyl-4-methoxy-3,5-dimethylpyridine hydrochloride was replaced by 0.01 mole of each of the corresponding pyridine compounds [IV].

2-[2-(3,5-Dimethyl)pyridylmethylthio]-5-(2,2,2-trifluoroethoxy)imidazo[4,5-b]pyridine, m.p. 173°–174° C.

2-[2-(3,4,5-Trimethyl)pyridylmethylthio]-6-(2,2,2-trifluoroethoxy)imidazo[4,5-b]pyridine, m.p. 145°–148° C.

2-[2-(4-Methoxy-5-methyl)pyridylmethylthio]-7-(2,2,2-trifluoroethoxy)imidazo[4,5-b]pyridine, m.p. 157°–159° C.

2-[2-(4-Methyl)pyridylmethylthio]-5-(2,2,3,3,4,4,4-heptafluorobutyloxy)imidazo[4,5-b]pyridine, glassy material.

2-[2-(3,5-Dimethyl)pyridylmethylthio]-5-n-pentyloxyimidazo[4,5-b]pyridine, m.p. 101°–103° C.

2-[2-(3,4,5-Trimethyl)pyridylmethylthio]-6-nhexyloxyimidazo[4,5-b]pyridine, m.p. 96°-99° C.

2-[2-(3,5-Dimethyl)pyridylmethylthio]-5-n-heptyloxyimidazo[4,5-b]pyridine, m.p. 119°-120° C.

2-[2-(3,5-Dimethyl)pyridylmethylthio]-5-(3-methylbutyloxy)imidazo[4,5-b]pyridine, m.p. 101°-104° C.

2-[2-(4-Methoxy-5-methyl)pyridylmethylthio]-7-(2,4,4trimethylpentyloxy)imidazo[4,5-b]pyridine, glassy material.

2-[2-(3,5-Dimethyl-4-methoxy)pyridylmethylthio]-6-(3-cyclopentylpropyloxy)imidazo[4,5-b]pyridine, glassy material.

2-[2-(4-Methyl)pyridylmethylthio]-7-cyclohexylmethyloxyimidazo[4,5-b]pyridine, glassy material.

EXAMPLE 1

1.50 g (0.005 mole) of 2-[2-(3,5-dimethyl)pyridylmethylthio]-5-methoxyimidazo[4,5-b]pyridine was dissolved in 150 ml of chloroform. To this solution was slowly added 0.86 g (0.005 mole) of m-chloroperbenzoic acid at 0°-5° C., followed by stirring at that temperature for 10 minutes. While the resulting reaction solution was being kept at 0°-5° C., 30 ml of a 5% aqueous solution of sodium hydrogen carbonate was injected thereinto and mixed therewith. Thereafter, the chloroform layer was separated, dried over anhydrous sodium sulfate, and then evaporated to dryness under reduced pressure. The resulting residue was recrystallized from ethyl acetate to obtain 1.18 g (74.7% yield) of 2-[2-(3,5-dimethyl)pyridylmethylsulfinyl]-5-methoxyimidazo[4,5-b]pyridine in the form of colorless crystals. This product had a melting point of 175°-177° C.

Infrared absorption spectrum (KBr, cm$^{-1}$): 1060(S=O).

Analysis: Calcd. for $C_{15}H_{16}N_4O_2S$ (%) C, 56.94; H, 5.10; N, 17.71. Found (%) C, 57.03; H, 5.04; N, 17.82.

EXAMPLES 2-37

The compounds listed in Table 5 were prepared in substantially the same manner as described in Example 1, except that the 2-[2-(3,5-dimethyl)pyridylmethylthio]-5-methoxyimidazo[4,5-b]pyridine (0.005 mole) was replaced by each of the corresponding sulfide compounds [II] (0.005 mole), and the reaction temperature and the reaction time were suitably modified. These compounds were obtained in a yield ranging from 72.4% to 90.8%.

TABLE 5

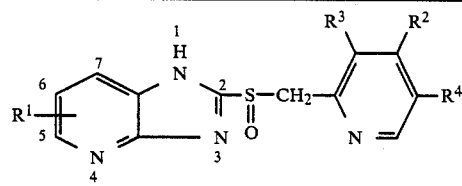

| Example No. | $R^1$ | $R^2$ | $R^3$ | $R^4$ | Melting point °C. (Recrystn. solvent) | IR(KBr)cm$^{-1}$ | Elemental analysis Molecular formula: upper row Calcd. (%) lower row Found (%) |
|---|---|---|---|---|---|---|---|
| 2 | 5-OCH$_3$ | OCH$_3$ | CH$_3$ | CH$_3$ | 174-175 (ethyl ether) | 1030 (S=O) | $C_{16}H_{18}N_4O_3S$: C,55.47 H,5.24 N,16.18 C,55.62 H,5.37 N,16.07 |
| 3 | 5-OCH$_3$ | CH$_3$ | CH$_3$ | CH$_3$ | 188-190 (acetonitrile-chloroform) | 1050 (S=O) | $C_{16}H_{18}N_4O_2S$: C,58.16 H,5.49 N,16.96 C,58.36 H,5.55 N,16.75 |
| 4 | 5-OCH$_3$ | OCH$_3$ | H | CH$_3$ | 180-184 (ethyl acetate) | 1030 (S=O) | $C_{15}H_{16}N_4O_3S$: C,54.20 H,4.85 N,16.86 C,54.12 H,4.96 N,16.68 |
| 5 | 5-OCH$_3$ | CH$_3$ | H | H | 139-141 (ethyl acetate) | 1050 (S=O) | $C_{14}H_{14}N_4O_2S$: C,55.61 H,4.67 N,18.53 C,55.79 H,4.78 N,18.48 |
| 6 | 6-OCH$_3$ | H | CH$_3$ | CH$_3$ | 163-166 (ethyl acetate) | 1050 (S=O) | $C_{15}H_{16}N_4O_2S$: C,56.94 H,5.10 N,17.71 C,56.76 H,5.25 N,17.59 |
| 7 | 7-OCH$_3$ | OCH$_3$ | H | CH$_3$ | 175-178 (ethyl acetate) | 1050 (S=O) | $C_{15}H_{16}N_4O_3S$: C,54.20 H,4.85 N,16.86 C,54.01 H,4.92 N,16.82 |
| 8 | 5-OC$_2$H$_5$ | CH$_3$ | CH$_3$ | CH$_3$ | 160-163 (ethyl acetate) | 1050 (S=O) | $C_{17}H_{20}N_4O_2S$: C,59.28 H,5.85 N,16.27 C,59.35 H,5.92 N,16.21 |
| 9 | 7-OC$_2$H$_5$ | CH$_3$ | CH$_3$ | CH$_3$ | 165-167 (ethyl acetate) | 1050 (S=O) | $C_{17}H_{20}N_4O_2S$: C,59.28 H,5.85 N,16.27 C,59.48 H,5.89 N,16.38 |
| 10 | 5-OCH(CH$_3$)$_2$ | H | CH$_3$ | CH$_3$ | 146-148 (methanol-ethyl ether) | 1040 (S=O) | $C_{17}H_{20}N_4O_2S$: C,59.28 H,5.85 N,16.27 C,59.49 H,5.80 N,16.27 |
| 11 | 5-OCHCH$_2$CH$_3$ \| CH$_3$ | CH$_3$ | H | H | glassy material (ethyl ether) | 1040 (S=O) | $C_{17}H_{20}N_4O_2S$: C,59.28 H,5.85 N,16.27 C,59.20 H,5.97 N,16.48 |
| 12 | 5-O—n-C$_4$H$_9$ | CH$_3$ | CH$_3$ | CH$_3$ | glassy material (ethyl ether) | 1040 (S=O) | $C_{19}H_{24}N_4O_2S$: C,61.26 H,6.49 N,15.04 C,61.54 H,6.51 N,15.11 |

TABLE 5-continued

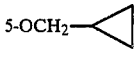

| Example No. | R¹ | R² | R³ | R⁴ | Melting point °C. (Recrystn. solvent) | IR(KBr)cm$^{-1}$ | Elemental analysis Molecular formula: upper row Calcd. (%) lower row Found (%) |
|---|---|---|---|---|---|---|---|
| 13 | 5-OCH₂—△ | OCH₃ | H | CH₃ | 154–157 (methanol-ethyl ether) | 1050 (S=O) | C₁₈H₂₀N₄O₃S: C,58.04 H,5.41 N,15.05 C,58.02 H,5.29 N,14.92 |
| 14 | 5-OC₂H₅ | H | CH₃ | CH₃ | 151–152 (ethyl acetate) | 1060 (S=O) | C₁₆H₁₈N₄O₂S: C,58.16 H,5.49 N,16.96 C,58.42 H,5.53 N,16.98 |
| 15 | 5-OCH(CH₃)₂ | OCH₃ | CH₃ | CH₃ | 124–126 (chloroform-ethyl ether) | 1060 1080 (S=O) | C₁₈H₂₂N₄O₃S: C,57.74 H,5.92 N,14.96 C,57.96 H,5.99 N,14.81 |
| 16 | 5-OCH(CH₃)₂ | OCH₃ | H | CH₃ | 169–173 (chloroform-ethyl ether) | 1040 (S=O) | C₁₇H₂₀N₄O₃S: C,56.65 H,5.59 N,15.54 C,56.54 H,5.45 N,15.60 |
| 17 | 5-OCH(CH₃)₂ | OCH₃ | H | H | 150–152 (chloroform-ethyl ether) | 1060 (S=O) | C₁₆H₁₈N₄O₃S: C,55.48 H,5.24 N,16.17 C,55.55 H,5.37 N,16.27 |
| 18 | 5-OCH₂CH₂CH₃ | H | CH₃ | CH₃ | 163–166 (ethyl acetate) | 1060 (S=O) | C₁₇H₂₀N₄O₂S: C,59.28 H,5.85 N,16.27 C,59.32 H,5.87 N,16.40 |
| 19 | 5-OCH₂CH(CH₃)₂ | H | CH₃ | CH₃ | 150–151 (ethyl acetate-hexane) | 1060 (S=O) | C₁₈H₂₂N₄O₂S: C,60.31 H,6.19 N,15.63 C,60.43 H,6.25 N,15.82 |
| 20 | 5-OCH₂CH(CH₃)₂ | OCH₃ | CH₃ | CH₃ | 160–161 (ethyl ether) | 1080 (S=O) | C₁₉H₂₄N₄O₃S: C,58.74 H,6.23 N,14.42 C,58.55 H,6.40 N,14.21 |
| 21 | 5-OCH₂CH(CH₃)₂ | OCH₃ | H | CH₃ | 142–144 (ethyl ether) | 1080 (S=O) | C₁₈H₂₂N₄O₃S: C,57.74 H,5.92 N,14.96 C,57.97 H,6.03 N,14.99 |
| 22 | 5-OCH₂CH(CH₃)₂ | OCH₃ | H | H | 157–159 (ethyl ether) | 1050 (S=O) | C₁₇H₂₀N₄O₃S: C,56.65 H,5.59 N,15.54 C,56.90 H,5.84 N,15.47 |
| 23 | 5-OCH₂—△ | H | CH₃ | CH₃ | 155–157 (chloroform-ethyl ether) | 1060 (S=O) | C₁₈H₂₀N₄O₂S: C,60.65 H,5.66 N,15.72 C,60.82 H,5.75 N,15.59 |
| 24 | 5-OCH₂—△ | OCH₃ | CH₃ | CH₃ | 150–154 (ethyl acetate) | 1060 1080 (S=O) | C₁₉H₂₂N₄O₃S: C,59.05 H,5.74 N,14.50 C,59.19 H,5.90 N,14.43 |
| 25 | 5-OCH₂—△ | OCH₃ | H | H | 149–151 (ethyl acetate) | 1040 (S=O) | C₁₇H₁₈N₄O₃S: C,56.97 H,5.06 N,15.63 C,57.20 H,5.21 N,15.62 |
| 26 | 5-OCH₂CF₃ | OCH₃ | CH₃ | CH₃ | 169–170 (ethyl acetate) | 1060 1080 (S=O) | C₁₇H₁₇N₄O₃SF₃: C,49.27 H,4.13 N,13.52 C,49.25 H,4.20 N,13.56 |
| 27 | 5-OCH₂CF₃ | H | CH₃ | CH₃ | 172–174 | 1070 | C₁₆H₁₅N₄O₂SF₃: |

TABLE 5-continued

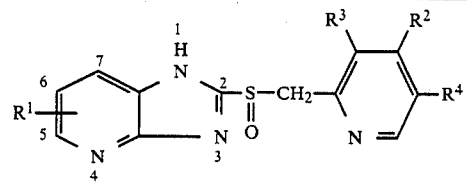

| Example No. | R¹ | R² | R³ | R⁴ | Melting point °C. (Recrystn. solvent) | IR(KBr)cm⁻¹ | Elemental analysis Molecular formula: upper row Calcd. (%) lower row Found (%) |
|---|---|---|---|---|---|---|---|
|  |  |  |  |  | (ethyl acetate) | (S=O) | C,50.00 H,3.93 N,14.58 C,50.21 H,4.01 N,14.51 |
| 28 | 6-OCH$_2$CF$_3$ | CH$_3$ | CH$_3$ | CH$_3$ | 165-168 (ethyl acetate) | 1060 (S=O) | C$_{17}$H$_{17}$N$_4$O$_2$SF$_3$: C,51.25 H,4.30 N,14.06 C,51.40 H,4.37 N,14.13 |
| 29 | 7-OCH$_2$CF$_3$ | OCH$_3$ | H | CH$_3$ | 159-162 (ethyl acetate) | 1060 (S=O) | C$_{16}$H$_{15}$N$_4$O$_3$SF$_3$: C,48.00 H,3.78 N,13.99 C,48.09 H,3.73 N,13.87 |
| 30 | 5-OCH$_2$(CF$_2$)$_2$CF$_3$ | CH$_3$ | H | H | colorless glassy material (ethyl ether) | 1070 (S=O) | C$_{17}$H$_{13}$N$_4$O$_2$SF$_7$: C,43.41 H,2.79 N,11.91 C,43.54 H,2.91 N,11.88 |
| 31 | 5-O(CH$_2$)$_4$CH$_3$ | H | CH$_3$ | CH$_3$ | 119-122 (dichloromethane-ethyl ether) | 1060 (S=O) | C$_{19}$H$_{24}$N$_4$O$_2$S: C,61.27 H,6.49 N,15.04 C,61.07 H,6.63 N,15.21 |
| 32 | 6-O(CH$_2$)$_5$CH$_3$ | CH$_3$ | CH$_3$ | CH$_3$ | 125-127 (dichloromethane) | 1060 (S=O) | C$_{21}$H$_{28}$N$_4$O$_2$S: C,62.97 H,7.05 N,13.99 C,62.78 H,7.01 N,14.12 |
| 33 | 5-O(CH$_2$)$_6$CH$_3$ | H | CH$_3$ | CH$_3$ | 126-127 (ethyl acetate) | 1070 (S=O) | C$_{21}$H$_{28}$N$_4$O$_2$S: C,62.97 H,7.05 N,13.99 C,63.20 H,6.99 N,13.83 |
| 34 | 5-O(CH$_2$)$_2$—CH(CH$_3$)$_2$ | H | CH$_3$ | CH$_3$ | 115-120 (ethyl ether) | 1070 (S=O) | C$_{19}$H$_{24}$N$_4$O$_2$S: C,61.27 H,6.49 N,15.04 C,61.33 H,6.62 N,15.17 |
| 35 | 7-OCH$_2$—CH(CH$_3$)—CH$_2$C(CH$_3$)$_3$ | OCH$_3$ | H | CH$_3$ | colorless glassy material (ethyl ether) | 1060 (S=O) | C$_{22}$H$_{30}$N$_4$O$_3$S: C,61.37 H,7.02 N,13.01 C,61.51 H,7.26 N,12.95 |
| 36 | 6-O(CH$_2$)$_3$-cyclopentyl | OCH$_3$ | CH$_3$ | CH$_3$ | colorless glassy material (ethyl ether) | 1070 (S=O) | C$_{23}$H$_{30}$N$_4$O$_3$S: C,62.42 H,6.83 N,12.66 C,62.19 H,6.75 N,12.78 |
| 37 | 7-OCH$_2$-cyclohexyl | CH$_3$ | H | H | colorless glassy material (ethyl ether) | 1070 (S=O) | C$_{20}$H$_{24}$N$_4$O$_2$S: C,62.48 H,6.29 N,14.57 C,62.64 H,6.17 N,14.34 |

Now the preparation of several pharmaceutical compositions containing the present compounds [I] will be described hereinbelow.

|  | % by weight |
|---|---|
| (1) Compound of Example 1 | 25.0 |
| (2) Lactose | 41.0 |
| (3) Corn starch | 15.0 |
| (4) Crystalline cellulose | 15.0 |
| (5) Hydroxypropyl cellulose | 3.0 |
| (6) Magnesium stearate | 1.0 |
|  | 100.0 |

The above ingredients (1)–(5) were blended together After the addition of water, the resulting mixture was granulated and then dried. The granules so formed were adjusted to a predetermined size range, and the ingredient (6) was added thereto. The resulting mixture was compressed to form tablets each containing 100 mg of the active ingredient.

|  | % by weight |
|---|---|
| (1) Compound of Example 24 | 25.0 |
| (2) Lactose | 50.0 |
| (3) Corn starch | 20.0 |
| (4) Hydroxypropyl cellulose | 3.0 |
| (5) Synthetic aluminum silicate | 1.0 |
| (6) Magnesium stearate | 1.0 |
|  | 100.0 |

According to conventional procedure, the above ingredients were blended together and then granulated. The granules so formed were filled into capsules, each of which contained 100 mg of the active ingredient.

What is claimed is:

1. An imidazo[4,5-b]pyridine compound of the formula

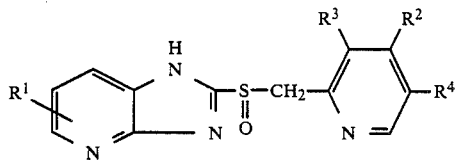

where R¹ is a straight-chain or branched alkoxy group of 1 to 8 carbon atoms which may be substituted with a cycloalkyl group of 3 to 6 carbon atoms or R¹ is a fluoroalkyloxy group of 2 to 4 carbon atoms, R² is a hydrogen atom, a methyl group or a methoxy group, and R³ and R⁴ are each a hydrogen atom or a methyl group and may be the same or different.

2. A compound as claimed in claim 1 wherein the straight-chain or branched alkoxy group is selected from the group consisting of methoxy, ethoxy, isopropyloxy, n-propyloxy, sec-butyloxy, isobutyloxy, n-butyloxy, n-pentyloxy, 3-methylbutyloxy, n-hexyloxy, n-heptyloxy, 2,4,4-trimethylpentyloxy, cyclopropylmethyloxy, 3-cyclopentylpropyloxy and cyclohexylmethyloxy.

3. A compound as claimed in claim 1 wherein the fluoroalkyloxy group is selected from the group consisting of 2,2,2-trifluoroethoxy and 2,2,3,3,4,4,4-heptafluorobutyloxy.

4. A compound as claimed in any one of claims 1 to 3 wherein the substituted pyridyl group represented by the formula

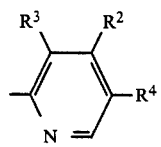

is selected from the group consisting of 2-(3,5-dimethyl)pyridyl, 2-(3,5-dimethyl-4-methoxy)pyridyl, 2-(3,4,5-trimethyl)pyridyl, 2-(4-methoxy-5-methyl)pyridyl, 2-(4-methoxy)pyridyl and 2-(4-methyl)pyridyl.

5. A compound as claimed in claim 1 which is any one of the following compounds,
2-[2-(3,5-dimethyl)pyridylmethylsulfinyl]-5-methoxyimidazo[4,5-b]pyridine,
2-[2-(3,5-dimethyl-4-methoxy)pyridylmethylsulfinyl]-5-methoxyimidazo[4,5-b]pyridine,
2-[2-(3,4,5-trimethyl)pyridylmethylsulfinyl]-5-methoxyimidazo[4,5-b]pyridine,
2-[2-(4-methoxy-5-methyl)pyridylmethylsulfinyl]-5-methoxyimidazo[4,5-b]pyridine,
2-[2-(4-methoxy-5-methyl)pyridylmethylsulfinyl]-7-methoxyimidazo[4,5-b]pyridine,
2-[2-(3,4,5-trimethyl)pyridylmethylsulfinyl]-5-ethoxyimidazo[4,5-b]pyridine,
2-[2-(3,5-dimethyl)pyridylmethylsulfinyl]-5-isopropyloxyimidazo[4,5-b]pyridine,
2-[2-(3,4,5-trimethyl)pyridylmethylsulfinyl]-5-n-butyloxyimidazo[4,5-b]pyridine,
2-[2-(4-methoxy-5-methyl)pyridylmethylsulfinyl]-5-cyclopropylmethyloxyimidazo[4,5-b]pyridine,
2-[2-(3,5-dimethyl)pyridylmethylsulfinyl]-5-ethoxyimidazo[4,5-b]pyridine,
2-[2-(3,5-dimethyl-4-methoxy)pyridylmethylsulfinyl]-5-isopropyloxyimidazo[4,5-b]pyridine,
2-[2-(4-methoxy-5-methyl)pyridylmethylsulfinyl]-5isopropyloxyimidazo[4,5-b]pyridine,
2-[2-(4-methoxy)pyridylmethylsulfinyl]-5-isopropyloxyimidazo[4,5-b]pyridine,
2-[2-(3,5-dimethyl)pyridylmethylsulfinyl]-5-n-propyloxyimidazo[4,5-b]pyridine,
2-[2-(3,5-dimethyl)pyridylmethylsulfinyl]-5-isobutyloxyimidazo[4,5-b]pyridine,
2-[2-(3,5-dimethyl-4-methoxy)pyridylmethylsulfinyl]-5-isobutyloxyimidazo[4,5-b]pyridine,
2-[2-(4-methoxy-5-methyl)pyridylmethylsulfinyl]-5isobutyloxyimidazo[4,5-b]pyridine,
2-[2-(4-methoxy)pyridylmethylsulfinyl]-5-isobutyloxyimidazo[4,5-b]pyridine,
2-[2-(3,5-dimethyl)pyridylmethylsulfinyl]-5-cyclopropylmethyloxyimidazo[4,5-b]pyridine,
2-[2-(3,5-dimethyl-4-methoxy)pyridylmethylsulfinyl]-5-cyclopropylmethyloxyimidazo[4,5-b]pyridine,
2-[2-(4-methoxy)pyridylmethylsulfinyl]-5-cyclopropylmethyloxyimidazo[4,5-b]pyridine,
2-[2-(3,5-dimethyl-4-methoxy)pyridylmethylsulfinyl]-5-(2,2,2-trifluoroethoxy)imidazo[4,5-b]pyridine,
2-[2-(4-methyl)pyridylmethylsulfinyl]-5-(2,2,3,3,4,4,4-heptafluorobutyloxy)imidazo[4,5-b]pyridine,
2-[2-(3,5-dimethyl)pyridylmethylsulfinyl]-5-n-heptyloxyimidazo[4,5-b]pyridine,
2-[2-(3,5-dimethyl)pyridylmethylsulfinyl]-5-(3-methylbutyloxy)imidazo[4,5-b]pyridine or
2-[2-(3,5-dimethyl-4-methoxy)pyridylmethylsulfinyl]-6-(3-cyclopentylpropyloxy)imidazo[4,5-b]pyridine.

6. A sulfide compound of the formula

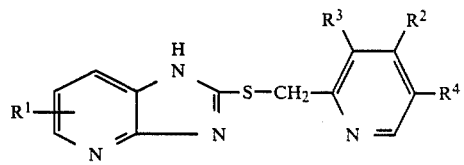

where R¹ is a straight-chain or branched alkoxy group of 1 to 8 carbon atoms which may be substituted with a cycloalkyl group of 3 to 6 carbon atoms, or R¹ is a fluoroalkyloxy group of 2 to 4 carbon atoms, R² is a hydrogen atom, a methyl group or a methoxy group, and R³ and R⁴ are each a hydrogen atom or a methyl group and may be the same or different.

7. A compound as claimed in claim 6 which is any one of the following compounds,
2-[2-(3,5-dimethyl)pyridylmethylthio]-5-methoxyimidazo[4,5-b]pyridine,
2-[2-(3,5-dimethyl-4-methoxy)pyridylmethylthio]-5-methoxyimidazo[4,5-b]pyridine,
2-[2-(3,4,5-trimethyl)pyridylmethylthio]-5-methoxyimidazo[4,5-b]pyridine,
2-[2-(4-methoxy-5-methyl)pyridylmethylthio]-5-methoxyimidazo[4,5-b]pyridine,
2-[2-(4-methyl)pyridylmethylthio]-5-methoxyimidazo[4,5-b]pyridine,
2-[2-(3,5-dimethyl)pyridylmethylthio]-6-methoxyimidazo[4,5-b]pyridine,
2-[2-(4-methoxy-5-methyl)pyridylmethylthio]-7-methoxyimidazo[4,5-b]pyridine,
2-[2-(3,4,5-trimethyl)pyridylmethylthio]-5-ethoxyimidazo[4,5-b]pyridine,
2-[2-(3,4,5-trimethyl)pyridylmethylthio]-7-ethoxyimidazo[4,5-b]pyridine, 2-[2-(3,5-dimethyl)pyridylmethylthio]-5-isopropyloxyimidazo[4,5-b]pyridine,
2-[2-(4-methyl)pyridylmethylthio]-5-sec-butyloxyimidazo[4,5-b]pyridine,
2-[2-(3,4,5-trimethyl)pyridylmethylthio]-5-n-butyloxyimidazo[4,5-b]pyridine,
2-[2-(4-methoxy-5-methyl)pyridylmethylthio]-5-cyclopropylmethyloxyimidazo[4,5-b]pyridine,
2-[2-(3,5-dimethyl)pyridylmethylthio]-5-ethoxyimidazo[4,5-b]pyridine,
2-[2-(3,5-dimethyl-4-methoxy)pyridylmethylthio]-5-isopropyloxyimidazo[4,5-b]pyridine,
2-[2-(4-methoxy-5-methyl)pyridylmethylthio]-5-isopropyloxyimidazo[4,5-b]pyridine,
2-[2-(4-methoxy)pyridylmethylthio]-5-isopropyloxyimidazo[4,5-b]pyridine,
2-[2-(3,5-dimethyl)pyridylmethylthio]-5-n-propyloxyimidazo[4,5-b]pyridine,
2-[2-(3,5-dimethy)pyridylmethylthio]-5-isobutyloxyimidazo[4,5-b]pyridine,
2-[2-(3,5-dimethyl-4-methoxy)pyridylmethylthio]-5-isobutyloxyimidazo[4,5-b]pyridine,
2-[2-(4-methoxy-5-methyl)pyridylmethylthio]-5-isobutyloxyimidazo[4,5-b]pyridine,
2-[2-(4-methoxy)pyridylmethylthio]-5-isobutyloxyimidazo[4,5-b]pyridine,
2-[2-(3,5-dimethyl)pyridylmethylthio]-5-cyclopropylmethyloxyimidazo[4,5-b]pyridine,
2-[2-(3,5-dimethyl-4-methoxy)pyridylmethylthio]-5-cyclopropylmethyloxyimidazo[4,5-b]pyridine,
2-[2-(4-methoxy)pyridylmethylthio]-5-cyclopropylmethyloxyimidazo[4,5-b]pyridine,
2-[2-(3,5-dimethyl-4-methoxy)pyridylmethylthio]-5-(2,2,2-trifluoroethoxy)imidazo[4,5-b]pyridine,
2-[2-(3,5-dimethyl)pyridylmethylthio]-5-(2,2,2-trifluoroethoxy)imidazo[4,5-b]pyridine,
2-[2-(3,4,5-trimethyl)pyridylmethylthio]-6-(2,2,2-trifluoroethoxy)imidazo[4,5-b]pyridine,
2-[2-(4-methoxy-5-methyl)pyridylmethylthio]-7-(2,2,2-trifluoroethoxy)imidazo[4,5-b]pyridine,
2-[2-(4-methyl)pyridylmethylthio]-5-(2,2,3,3,4,4,4-heptafluorobutyloxy)imidazo[4,5-b]pyridine,
2-[2-(3,5-dimethyl)pyridylmethylthio]-5-n-pentyloxyimidazo[4,5-b]pyridine,
2-[2-(3,4,5-trimethyl)pyridylmethylthio]-6-n-hexyloxyimidazo[4,5-b]pyridine,
2-[2-(3,5-dimethyl)pyridylmethylthio]-5-n-heptyloxyimidazo[4,5-b]pyridine,
2-[2-(3,5-dimethyl)pyridylmethylthio]-5-(3-methylbutyloxy)imidazo[4,5-b]pyridine,
2-[2-(4-methoxy-5-methyl)pyridylmethylthio]-7-(2,4,4-trimethylpentyloxy)imidazo[4,5-b]pyridine,
2-[2-(3,5-dimethyl-4-methoxy)pyridylmethylthio]-6-(3-cyclopentylpropyloxy)imidazo[4,5-b]pyridine or
2-[2-(4-methyl)pyridylmethylthio]-7-cyclohexylmethyloxyimidazo[4,5-b]pyridine.

8. A pharmaceutical composition having anti-ulcer activity comprising an effective daily dose of 0.5 to 2000 mg of an imidazo[4,5-b]pyridine compound of claim 1 and one or more physiological harmless pharmaceutical carriers.

9. A pharmaceutical composition as claimed in claim 8 where the effective daily dose is an amount of 3 to 200 mg.

10. A pharmaceutical composition as claimed in claim 8 or 9 where the imidazo[4,5-b]pyridine compound of claim 1 is selected from the group consisting of
2-[2-(3,5-dimethyl)pyridylmethylsulfinyl]-5-methoxyimidazo[4,5-b]pyridine,
2-[2-(3,5-dimethyl-4-methoxy)pyridylmethylsulfinyl]-5-methoxyimidazo[4,5-b]pyridine,
2-[2-(3,4,5-trimethyl)pyridylmethylsulfinyl]-5-methoxyimidazo[4,5-b]pyridine,
2-[2-(4-methoxy-5-methyl)pyridylmethylsulfinyl]-5-methoxyimidazo[4,5-b]pyridine,
2-[2-(4-methoxy-5-methyl)pyridylmethylsulfinyl]-7-methoxyimidazo[4,5-b]pyridine,
2-[2-(3,4,5-trimethyl)pyridylmethylsulfinyl]-5-ethoxyimidazo[4,5-b]pyridine,
2-[2-(3,5-dimethyl)pyridylmethylsulfinyl]-5-isopropyloxyimidazo[4,5-b]pyridine,
2-[2-(3,4,5-trimethyl)pyridylmethylsulfinyl]-5-n-butyloxyimidazo[4,5-b]pyridine,
2-[2-(4-methoxy-5-methyl)pyridylmethylsulfinyl]-5-cyclopropylmethyloxyimidazo[4,5-b]pyridine,
2-[2-(3,5-dimethyl)pyridylmethylsulfinyl]-5-ethoxyimidazo[4,5-b]pyridine,
2-[2-(3,5-dimethyl-4-methoxy)pyridylmethylsulfinyl]-5-isopropyloxyimidazo[4,5-b]pyridine,
2-[2-(4-methoxy-5-methyl)pyridylmethylsulfinyl]-5-isopropyloxyimidazo[4,5-b]pyridine,
2-[2-(4-methoxy)pyridylmethylsulfinyl]-5-isopropyloxyimidazo[4,5-b]pyridine,
2-[2-(3,5-dimethyl)pyridylmethylsulfinyl]-5-n-propyloxyimidazo[4,5-b]pyridine,
2-[2-(3,5-dimethyl)pyridylmethylsulfinyl]-5-isobutyloxyimidazo[4,5-b]pyridine,
2-[2-(3,5-dimethyl-4-methoxy)pyridylmethylsulfinyl]-5-isobutyloxyimidazo[4,5-b]pyridine,
2-[2-(4-methoxy-5-methyl)pyridylmethylsulfinyl]-5-isobutyloxyimidazo[4,5-b]pyridine,
2-[2-(4-methoxy)pyridylmethylsulfinyl]-5-isobutyloxyimidazo[4,5-b]pyridine,
2-[2-(3,5-dimethyl)pyridylmethylsulfinyl]-5-cyclopropylmethyloxyimidazo[4,5-b]pyridine,
2-[2-(3,5-dimethyl-4-methoxy)pyridylmethylsulfinyl]-5-cyclopropylmethyloxyimidazo[4,5-b]pyridine,
2-[2-(4-methoxy)pyridylmethylsulfinyl]-5-cyclopropylmethyloxyimidazo[4,5-b]pyridine,
2-[2-(3,5-dimethyl-4-methoxy)pyridylmethylsulfinyl]-5-(2,2,2-trifluoroethoxy)imidazo[4,5-b]pyridine,
2-[2-(4-methyl)pyridylmethylsulfinyl]-5-(2,2,3,3,4,4,4-heptafluorobutyloxy)imidazo[4,5-b]pyridine,
2-[2-(3,5-dimethyl)pyridylmethylsulfinyl]-5-n-heptyloxyimidazo[4,5-b]pyridine,
2-[2-(3,5-dimethyl)pyridylmethylsulfinyl]-5-(3-methylbutyloxy)imidazo[4,5-b]pyridine and
2-[2-(3,5-dimethyl-4-methoxy)pyridylmethylsulfinyl]-6-(3-cyclopentylpropyloxy)imidazo[4,5-b]pyridine.

11. A method of using an imidazo[4,5-b]pyridine compound of claim 1 for treating gastric or duodenal ulcer in a living subject which comprises administering to such a subject a therapeutically effective amount of such compound of claim 1.

12. A method as claimed in claim 11 where the therapeutically effective amount is an amount of 0.5 to 200 mg per day.

13. A method as claimed in claim 11 or 12 where the imidazo[4,5-b]pyridine compound is selected from the group consisting of
2-[2-(3,5-dimethyl)pyridylmethylsulfinyl]-5-methoxyimidazo[4,5-b]pyridine,
2-[2-(3,4,5-trimethyl)pyridylmethylsulfinyl]-5-ethoxyimidazo[4,5-b]pyridine,
2-[2-(4-methoxy-5-methyl)pyridylmethylsulfinyl]-5-cyclopropylmethyloxyimidazo[4,5-b]pyridine,
2-[2-(3,5-dimethyl-4-methoxy)pyridylmethylsulfinyl]-5-cyclopropylmethyloxyimidazo[4,5-b]pyridine,
2-[2-(3,5-dimethyl-4-methoxy)pyridylmethylsulfinyl]-5-(2,2,2-trifluoroethoxy)imidazo[4,5-b]pyridine and
2-[2-(3,5-dimethyl)pyridylmethylsulfinyl]-5-n-heptyloxyimidazo[4,5-b]pyridine.

* * * * *